US 6,750,963 B2

(12) United States Patent
Sampas

(10) Patent No.: US 6,750,963 B2
(45) Date of Patent: Jun. 15, 2004

(54) IMAGING SYSTEMS FOR SIGNALS ON A SURFACE

(75) Inventor: Nicholas M. Sampas, San Jose, CA (US)

(73) Assignee: Agilent Technologies, Inc., Palo Alto, CA (US)

( * ) Notice: Subject to any disclaimer, the term of this patent is extended or adjusted under 35 U.S.C. 154(b) by 13 days.

(21) Appl. No.: 10/153,128

(22) Filed: May 21, 2002

(65) Prior Publication Data

US 2003/0218746 A1 Nov. 27, 2003

(51) Int. Cl.⁷ .............................................. G01N 21/64
(52) U.S. Cl. ..................... 356/318; 356/417; 356/458.1
(58) Field of Search ................. 356/317, 318, 356/417; 250/458.1, 459.1, 461.1, 461.2; 436/172

(56) References Cited

U.S. PATENT DOCUMENTS

| 5,563,710 A | 10/1996 | Webb et al. |
| 5,585,639 A | 12/1996 | Dorsel et al. |
| 5,631,734 A | 5/1997 | Stern et al. |
| 5,812,272 A | 9/1998 | King et al. |
| 5,900,949 A | 5/1999 | Sampas |
| 6,208,411 B1 * | 3/2001 | Vaez-Iravani ............ 356/237.2 |

FOREIGN PATENT DOCUMENTS

| WO | WO 97/43611 | 11/1997 | |
| WO | WO 00/58715 | * 10/2000 | .......... G01N/21/64 |

* cited by examiner

*Primary Examiner*—F. L. Evans

(57) ABSTRACT

Apparatus and methods are disclosed for imaging surfaces that comprise a sample. One embodiment of the present invention is an imaging apparatus comprising a holder for a surface, a light source adapted to illuminate the surface, a diffractive element between the holder and the light source and an imaging detector adapted to receive light from the surface. In a method for imaging a surface comprising a plurality of discrete features, light is selectively diffracted on to one or more predetermined features of the surface at a predetermined point in time. This step is repeated until substantially all of the features on the surface are illuminated. Light is detected from the surface to thereby image the surface.

21 Claims, 2 Drawing Sheets

IMAGING SYSTEMS FOR SIGNALS ON A SURFACE

BACKGROUND OF THE INVENTION

1. Field of the Invention

This invention relates to methods and apparatus for the imaging of marked materials associated with the surface of a substrate. In particular, the invention relates to methods and apparatus for imaging arrays of polymer sequences such as oligonucleotide arrays.

Biological assays involving fluorescent label molecules or scattering structures to detect, quantify or identify target chemical species bound to surfaces use optical detection and imaging systems. Arrays of different chemical probe species provide methods of highly parallel detection, and hence improved speed and efficiency, in assays. These arrays are sometimes referred to as chip or microarray technologies.

One method for detecting nucleic acids is to employ nucleic acid probes that have sequences complementary to the target nucleic acid sequences. A nucleic acid probe may be, or may be capable of being, labeled with a reporter group or may be, or may be capable of becoming, bound to a support. The detection of its signal depends upon the nature of the label or reporter group. Usually, the probe is comprised of natural nucleotides, such as ribonucleotides and deoxyribonucleotides and their derivatives, although unnatural nucleotide mimetics such as 2'-modified nucleosides, peptide nucleic acids and oligomeric nucleoside phosphonates are also used. Commonly, binding of the probes to the target is detected by means of a label incorporated into the probe. Alternatively, the probe may be unlabeled and the target nucleic acid labeled. Binding can be detected by separating the bound probe or target from the free probe or target and detecting the label. In one approach, a sandwich is formed comprised of one probe, which may be labeled, the target and a probe that is or can become bound to a surface. Alternatively, binding can be detected by a change in the signal-producing properties of the label upon binding, such as a change in the emission efficiency of a fluorescent or chemiluminescent label. This permits detection to be carried out without a separation step. Finally, binding can be detected by labeling the target, allowing the target to hybridize to a surface-bound probe, washing away the unbound target and detecting the labeled target that remains.

Direct detection of labeled target nucleic acid hybridized to surface-bound polynucleotide probes is particularly advantageous if the surface contains a mosaic of different probes that are individually localized to discrete, known areas of the surface. Such ordered arrays containing a large number of oligonucleotide probes have been developed as tools for high throughput analyses of genotype and gene expression. Oligonucleotides synthesized on a solid support recognize uniquely complementary nucleic acids by hybridization, and arrays can be designed to define specific target sequences, analyze gene expression patterns or identify specific allelic variations.

In one approach, cell matter is lysed, to release its DNA as fragments, which are then separated out by electrophoresis or other means, and then tagged with a fluorescent or other label. The resulting DNA mix is exposed to an array of oligonucleotide probes, whereupon selective attachment to matching probe sites takes place. The array is then washed and imaged so as to reveal for analysis and interpretation the sites where attachment occurred.

These chip technologies, such as DNA arrays and protein matrix arrays, need to be scanned to measure the number densities of labeled molecules and hence the concentration of target (or probe) molecules in solution. This sensing process is accomplished by means of a fluorescence imaging system. In order to reduce the deleterious effects of background from either the slide substrate (such as the glass slide) or the solution (assuming a wet-scanning system), confocal scanning systems are employed resulting in increased performance.

Confocal microscopes generally employ a pinhole that is confocal with an illuminated spot on a specimen to reject light that is not reflected or emitted from objects in the focal plane. This rejection of out-of-focus light enables the microscope to collect and combine a series of optical slices at different focus positions to generate a two or three-dimensional representation of the specimen. However, confocal microscopes tend to be complex devices with many moving parts. These moving parts often involve expensive high-precision stages necessitated by high-resolution scanning. A scanner with such high-precision stages will typically cost tens, and even hundreds, of thousands of dollars.

Optical scanning imaging techniques are employed in devices such as scanning laser microscopes, confocal scanning laser microscopes, tandem scanning confocal microscopes, scanning laser ophthalmoscopes and flying spot television devices. Confocal imaging systems can provide enhancements in contrast and in dynamic range. Certain of these imaging systems include moving optical elements for deflecting a laser beam so that an illumination spot is swept across the object to be scanned. Other such systems employ mechanical elements to rotate and illuminated pinhole for the same purpose. In the tandem scanning confocal microscopes a plurality of illumination spots is moved simultaneously to provide source multiplexing, necessary because the source does not have the higher radiance of a laser.

There is a need for a simple high-resolution scanner with a reduced number of moving parts. Ideally, the number of moving parts is one or fewer and the motion of any moving parts is simple.

2. Brief Description of Related Art

Webb, et al., (U.S. Pat. No. 5,563,710) discuss an imaging system with confocally self-detecting laser.

Stem, et al., (U.S. Pat. No. 5,631,734) discuss a method and apparatus for detection of fluorescently labeled materials.

Apparatus and method with tiled light source array for integrated array sensing is described in U.S. Pat. No. 5,812,272 (King, et al.).

U.S. Pat. No. 5,900,949 (Sampas) discloses a CCD imager for confocal scanning microscopy.

An optical scanning apparatus is discussed by Dorsel, et al., in U.S. Pat. No. 5,585,639.

Systems and methods for detection of labeled materials are disclosed in WO 97/43611 (Stern).

SUMMARY OF THE INVENTION

One embodiment of the present invention is an imaging apparatus comprising a holder for a surface, a light source adapted to illuminate the surface, a diffractive element between the holder and the light source and an imaging detector adapted to receive light from the surface.

Another embodiment of the present invention is a method for imaging a surface comprising a plurality of discrete features. Light is selectively diffracted on to one or more predetermined features of the surface at a predetermined point in time. This step is repeated until substantially all of the features on the surface are illuminated. Light is detected from the surface to thereby image the surface.

DEFINITIONS

Figure 1:
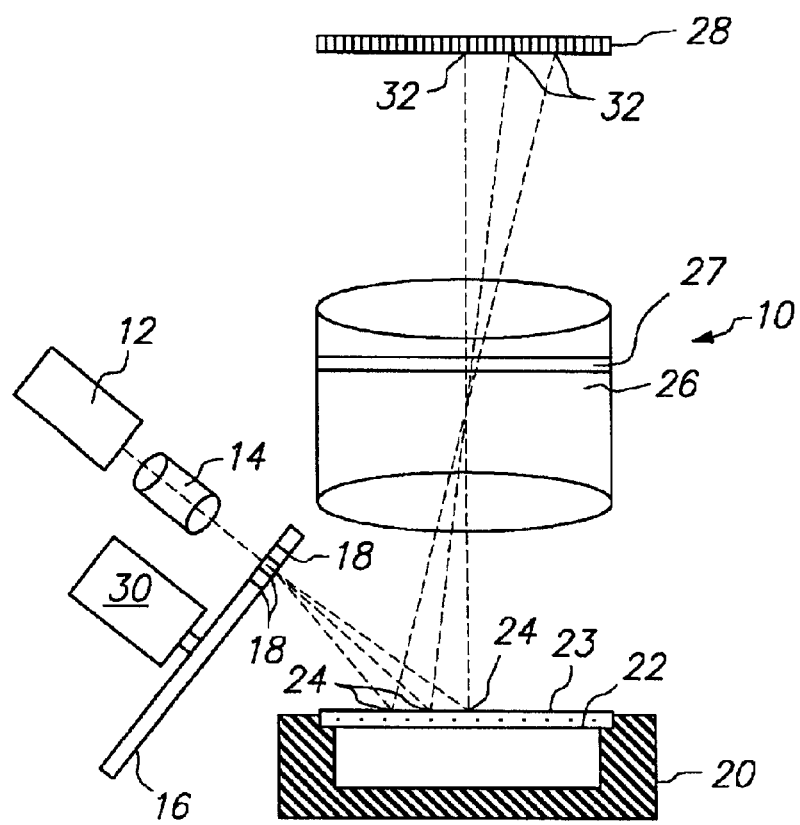
FIG. 1 is a diagrammatic sketch showing an embodiment of an apparatus in accordance with the present invention.

Before proceeding further with a description of the specific embodiments of the present invention, a number of terms will be defined.

A "target" is a molecule that has an affinity for a given probe. Targets may be naturally occurring or synthetic. The target may be, by way of example, antibodies, cell membrane receptors, monoclonal antibodies and antisera reactive with specific antigenic determinants, drugs, polynucleotides, nucleic acids, peptides, cofactors, lectins, sugars, polysaccharides, cells, cellular membranes and organelles.

A "probe" is a molecule recognized by a particular target. The probe may be one of the molecules mentioned above under the definition of target.

A "polynucleotide" is a compound or composition that is a polymeric nucleotide or nucleic acid polymer. The polynucleotide may be a natural compound or a synthetic compound. In the context of an assay, the polynucleotide is often referred to as a polynucleotide analyte. The polynucleotides include nucleic acids, and fragments thereof, from any source in purified or unpurified form including DNA (dsDNA and ssDNA) and RNA, including tRNA, mRNA, rRNA, t-RNA, mitochondrial DNA and RNA, chloroplast DNA and RNA, DNA/RNA hybrids, or mixtures thereof, genes, chromosomes, plasmids, the genomes of biological material such as microorganisms, e.g., bacteria, yeasts, viruses, viroids, molds, fungi, plants, animals, humans, and the like. The polynucleotide can be only a minor fraction of a complex mixture such as a biological sample. Also included are genes, such as hemoglobin gene for sickle-cell anemia, cystic fibrosis gene, oncogenes, cDNA, and the like.

The polynucleotide can be obtained from various biological materials by procedures well known in the art. The polynucleotide, where appropriate, may be cleaved to obtain a fragment that contains a target nucleotide sequence, for example, by shearing or by treatment with a restriction endonuclease or other site specific chemical cleavage method.

A "target nucleotide sequence" is a sequence of nucleotides to be identified, usually existing within a portion or all of a polynucleotide, usually a polynucleotide analyte. The identity of the target nucleotide sequence generally is known to an extent sufficient to allow preparation of various sequences hybridizable with the target nucleotide sequence and of oligonucleotides, such as probes and primers, and other molecules necessary for conducting methods in accordance with the present invention, an amplification of the target polynucleotide, and so forth.

An "oligonucleotide" is a polynucleotide, usually single stranded, usually a synthetic polynucleotide but may be a naturally occurring polynucleotide. The oligonucleotide(s) are usually comprised of a sequence of at least 5 nucleotides, preferably, 10 to 100 nucleotides, more preferably, 20 to 50 nucleotides, and usually 10 to 30 nucleotides, more preferably, 15 to 30 nucleotides.

An "oligonucleotide probe" is an oligonucleotide employed to bind to a portion of a polynucleotide such as another oligonucleotide or a target nucleotide sequence. The design and preparation of the oligonucleotide probes are generally dependent upon the sensitivity and specificity required, the sequence of the target polynucleotide and, in certain cases, the biological significance of certain portions of the target polynucleotide sequence.

A "nucleotide" is a base-sugar-phosphate combination that is the monomeric unit of nucleic acid polymers, i.e., DNA and RNA. The nucleotide may be natural or synthetic. The term "nucleotide" as used herein includes modified nucleotides that contain a modified base, sugar or phosphate group.

A "label" or "reporter molecule" or "reporter group" is a moiety that is capable of being activated usually by light and of producing a detectable light signal such as in, for example, fluorescence, phosphorescence, and so forth. The label can be a fluorescent group, preferably having a large Stokes shift, such as fluorescein, rhodamine, dichlorofluorescein, hexachlorofluorescein, tetramethylrhodamine, indocarbocyanine dyes such as Cy3™, Cy5™, Cy7™, and so forth, Texas Red, ethidium bromide, chelated lanthanides, phycoerythrin, GFP, and the like. Other types of labels include, for example, quantum dot particles and other dye particles, such as those involving fluorescence resonance energy transfer, and so forth. Usually, the label is part of a target nucleotide sequence or an oligonucleotide probe, either being conjugated thereto or otherwise bound thereto or associated therewith.

An "array" is an arrangement of features or objects in space in which each object occupies a separate predetermined spatial position. Typically, the objects have a predetermined arrangement in the x-axis and the y-axis, thus forming rows and columns. The arrays are generally formed on the surface of a substrate. For arrays, the surface of the substrate can comprise from about $10^2$ to about $10^8$ different features such as attached polynucleotides, each in an area of from about 2 micron by 2 micron to about 500 micron by 500 micron.

DETAILED DESCRIPTION OF THE INVENTION

The apparatus of the present invention are simple high-resolution imaging apparatus with one or less moving parts. The imaging apparatus can be implemented either in a scanning confocal arrangement or in a non-confocal arrangement. Briefly, light from a light source system is directed through a diffractive element and is focussed onto and scanned across the sample with sufficient resolution to resolve individual features on a surface. The light from the surface is collected, e.g., by an objective lens or other light collection device, and directed onto an imaging detector. The apparatus of the invention are much less expensive than known apparatus. The use of a low-cost diffractive element and a low-cost high precision motor to drive the diffractive element obviates the need for a very costly high precision x,y stages and the like.

The invention has particular application in the area of analysis of targets using arrays. However, this should not be construed as a limitation of the present invention, which has application in general to imaging a surface having a plurality of target features. The surface can be designed to have as few as two sites or as many as hundreds of thousands or millions of sites. The sites may be of any shape, preferably, square or rectangular, or circular for maximizing their area. The size of a site can be varied and can be of any size, usually in the range from about 2 square microns to about 2 square millimeters, preferably, in the range of about 5 to about 500 square microns. The spacing between sites on the device is determined by the ease of fabrication, the requirement for resolution between the various sites, and the number of sites desired on a device. However, particular spacing between sites or special arrangement or geometry of the sites is not necessary for device function.

The present apparatus comprise a holder for an optical surface. The surface is usually present on a substrate. The substrate can have any one of a number of shapes, such as a circle, square, rectangle, triangle, strip, plate, disk, rod, particle, including bead, and the like. The most cost-effective of these, in terms of manufacturing, is a square or rectangle. The substrate may be substantially planar or it may have one of a variety of alternative surface configurations. For example, the substrate may contain raised or depressed regions on which a sample is located. The substrate and its surface preferably form a rigid support on which the sample can be formed or places or the like. The substrate may be a slide such as a microscope slide or an array element, or it may be part of or all of a reaction chamber of, for example, a flow cell or a capillary device such as a capillary electrophoresis device or a "lab-on-a-chip" device. In the above instances, the slide or reaction chamber comprises the surface.

The substrate is usually constructed from any material that is compatible with the fluids with which a surface of the substrate comes into contact. Usually, the substrate is composed of a porous or non-porous water insoluble material. The substrate can be hydrophilic or capable of being rendered hydrophilic and includes inorganic materials such as glass, silica, fused silica, magnesium sulfate, and alumina; natural polymeric materials, synthetic or modified naturally occurring polymers, such as poly (vinyl chloride), polyacrylamide, polyacrylate, polyethylene, polypropylene, poly(4-methylbutene), polystyrene, polymethacrylate, poly (ethylene terephthalate), nylon, poly(vinyl butyrate), etc.; either used by themselves or in conjunction with other materials; glass available as Bioglass, ceramics, metals, and the like. Other substrate materials will be readily apparent to those of skill in the art in light of the disclosure herein. The substrate may be rigid or flexible. The substrate may be, for example, in the form of a semiconductor substrate or printed circuit board constructed from silicon or glass. The surface may be composed of the same material as the substrate or may be composed of a different material. For fluorescent labeling, materials with the least native fluorescence, such as glass, fused silica, or silicon allow the best sensitivity. Transparency of the substrate is also useful for "through-the-glass" excitation or detection geometries.

The nature of the holder for the surface depends on the nature of the substrate or support. In one embodiment the holder is a platform or a stage, usually flat, on which the surface rests. The holder may further comprise means for securing the substrate to the holder. This may be accomplished by the use of corresponding mating elements such as a cavity in the holder and a protrusion in the substrate. Alternatively, the substrate may be physically attached to the holder by, for example, screws, clips or other mounting techniques. The holder may be stationary or movable. When movable, the holder may be moved by means of a motor or the like in either the horizontal or vertical direction or both. A controller such as an appropriately programmed computer may control movement of the holder. The computer may be the same computer that receives, compiles and stores input from the apparatus as discussed hereinbelow.

The apparatus of the present invention further comprise a light source system adapted to illuminate the surface. In general, the light source system includes one or more sources of excitation radiation. Examples of a suitable light source, by way of illustration and not limitation, are an LED, laser diode, laser such as argon, heliumneon, diode, dye titanium sapphire, frequency-doubled diode pumped Nd:YAG and krypton, or VCEL. Typically, the excitation source illuminates the sample with an excitation wavelength that is within the visible spectrum, but other wavelengths such as near ultraviolet or near infrared spectrum may be used depending on the nature of labels employed, the nature of the sample to be analyzed, the number of different dyes used in the system, and the like. In some instances, excitation is with electromagnetic radiation having a wavelength at or near the absorption maximum of the label.

In one embodiment of the invention the apparatus comprise more than one source of excitation radiation or, in other words, a plurality of light sources such as an array of light sources. In this embodiment the light source system comprises 2 to about 100,000, usually, about 10 to about 10,000, light sources. Each of the light sources in the plurality of light sources is usually the same but need not be. The array of light sources has the light sources arranged in a predetermined pattern such as a certain number of light sources in rows and columns, for example, a 50×50 array, or one-dimensional such as a 1000×1 array. The nature of the arrangement in a plurality of light sources is dependent on the ease and scalability of manufacturing processes for the light source array. Furthermore, an important advantage of this invention is that any arbitrary light source geometry can be mapped to any other arbitrary biological array geometry so that each can be manufactured by the most economical methods.

In one embodiment the light source system is a laser source that is an N×M scannable microlaser array where N and M are typically in the range of about 1 to about 1000. In one approach the laser source is a 5×5 matrix of microlasers, addressable in row—column fashion, each having a coherence length of approximately 70 mm. However, microlaser arrays of varying sizes and of varying coherence lengths can be employed in the light source system.

A diffractive element lies between the light source and the holder for the substrate. The diffractive element comprises a plurality of small openings or diffraction gratings. The gratings may be of any shape such as circle, square, rectangle, triangle, and the like. The cross-sectional dimension of the diffraction gratings is dependent on the resolution required for scanning the substrate and the distances between the optical components and is usually about 5 $\mu$m to about 1000 $\mu$m, more usually, about 10 to about 50 microns. The cross-sectional dimension is measured from farthest opposing points on a cross-section of the opening of the diffractive element. For example, for an opening that is circular, the cross-sectional dimension is the diameter of the circle. In another example, the opening has a square cross-section and the dimension is measured from opposing corners of the square. The number of openings in the diffractive element is dependent on the number of features on the surface to be illuminated and on how many pixels are required per feature. For example, 1 is greater than or equal to the number of pixels per feature, which in turn is greater than 1000. In current instruments this is between 10,000 features and 1,000,000 features. For diagnostic applications this could be between 20 features and 1000 features. Usually, the number of openings is about 100 to about 1,000,000, more usually, about 1000 to about 100,000. In one embodiment the diffractive element comprises an array of openings where the openings are arranged in a predetermined pattern.

The combination of a plurality of light sources such as an array of light sources and a diffractive element with a plurality of openings such as an array of openings results in a number of advantages for the apparatus of the present invention. The combination can effectively eliminate pixels in an array. This means that any arbitrary geometry can be addressed in any order. There is no need for adjacent pixels to be addressed sequentially.

In one embodiment, the diffractive element is movable. For example, the diffractive element may be driven by a motor that is controlled, for example, by a microprocessor as discussed above for the movable holder. In this embodiment the element may take the form of a spinning disk, a rotating drum, a rectilinear array, and the like. The simplest and most economical and easiest to manufacture of these is a spinning disk. In another embodiment the diffractive element is stationary. Accordingly, a number of approaches for illuminating a surface are possible. In one approach, a beam of light from a light source is incident upon a small region comprising a number of openings or on a single opening of the diffractive element. The beam can be scanned from one region or opening of the diffractive element to another, for example, by moving the diffractive element itself. In another approach, the beam can be scanned across a stationary diffractive element. Alternatively, a combination of the above may be employed. Furthermore, in another approach different openings of the diffractive element can be sequentially illuminated with an array of sources. Each of the openings or small regions of the diffractive element corresponds to one or more pixel elements on the surface that is illuminated.

In one embodiment the diffractive element is a disk that is spun on its axis or rotated so that the light diffracted by the disk at any given point in time illuminates one or more discrete regions of the sample (not necessarily having cylindrical symmetry). As the disk advances from one diffractive region to the next, a new region or set of regions within the sample on the surface are illuminated sequentially. These illuminated regions need not be addressed in any particular order, as long as the relationship between regions illuminated and the corresponding relationship between the regions detected is maintained while reading out the results of the irradiation. In this way, the diffractive element can be arranged to illuminate a number of separate pixel regions of a sample on the surface at one instant, then in the next instant another set of different regions are illuminated simultaneously, etc, until the whole surface is scanned.

In an embodiment where a spinning disk is driven by a motor equipped with an optical encoder, then the encoder pulses indicating the absolute position of the disk can be used to signal the microprocessor which region on the surface is illuminated for read-out. This approach, when combined with, for example, a random access type array, such as a CMOS array, can achieve Z-axis (normal to the surface) discrimination sufficient for confocal scanning. The proper synchronization between the illumination of the surface and the readout of the surface is critical for proper function and is readily understood by those skilled in the art.

The advantage of this approach is that it allows the use of a low cost apparatus to map (or transform) the motion of the apparatus to any arbitrary geometry of the sample on a surface such as on a rectilinear slide. For example, the diffractive element may simply be a spinning disk mounted on a simple DC motor, perhaps with a high-resolution linear encoder. The spinning disk can then map the beam across an entire two-dimensional rectilinear slide. Each position of the motor could then correspond to one or more regions in a two-dimensional matrix within the slide. Thus, there should be sufficient addresses within the one-dimensional system for each address (pixel) on the two dimensional array. Nevertheless, as a single high-precision DC motor is far less costly than two precision translation stages, a large part of the cost associated with the imaging system could be saved. This also means that every feature of a two-dimensional sample could be addressed independently by an imaging system with only a single degree of freedom.

In another embodiment, for example, the sensing array is one-dimensional. Light may be diffracted in such a way that it moves from point to point on the sample slide in discrete steps. The points addressed sequentially in time need not necessarily be arranged in consecutive spatial locations on the sample. If the detector is a single element that collects light corresponding to multiple locations where the beam impinges on the sample, then the timing of the illumination will determine the identity of each region for which the light is collected. If the detector is an array, then the array is read out in the same sequence as those regions illuminated by the apparatus in a synchronized manner. Alternatively, if the detector is a linear array, then the illumination of the array could be along a uniform line that maps directly to the array detector.

If two-dimensional scanning is desired, then there are several approaches. Most conventional rectilinear scanners use one approach. In this approach, the sample is advanced using a relatively slow mechanical stage (slow-axis), while another actuator scans rapidly in an orthogonal direction. In this case, a detector either is exposed for subsequent read out or for read out on-the-fly, which means that an array sensor would synchronously detect emission while each pixel is illuminated. This approach yields a two-dimensional scan. The sample or the diffractive element can be advanced by a linear actuator, by a galvanometer, or by spinning the sample about its axis, such as the case for spinning disk or drum-shaped slide. Another approach for two-dimensional scanning involves a slow axis (or degree of freedom) and a fast axis (or degree of freedom). Either the sample of the diffractive array can be advanced in the slow axis while the diffractive array is advanced rapidly in the fast axis.

The diffractive element can be constructed in any one of a number of ways. In one approach holography is employed using interfering laser beams to expose a surface emulsion. To this end an interference pattern is produced within the emulsion that can reconstruct one of the original beams by the use of a single beam. This would require a series of exposures, one for each pixel or opening of the diffractive device. Another approach involves assembly of a large number of small diffractive elements. In this approach a large diffraction grating(s) is cut into pieces, which are reassembled into the appropriate geometry. An important requirement for this latter approach is that a large number of elements must be aligned precisely. Micro-fabrication of thinned metal lines that are moved electrostatically to make the diffraction grating may be employed; this replication technique is well known to those skilled in the art. Other approaches include laser etching, machining, and replication of a grating made by one of the other methodologies.

The present apparatus optionally comprise a lens between the light source system and the diffractive element. The lens functions to focus each light source onto each respective diffractive opening. The lens may be, for example, a compound lens such as a microscope objective or a simple lens or lens array, if an array light source is used.

The present apparatus optionally comprise a filter, such as, for example, a spatial filter, between the lens and the diffractive element. The filter functions to improve the profile of the beam of illuminating light from the light source. In addition, the filter may be a combination of lenses and a pinhole or a Fabry-Perot Cavity, which is an interferometric filter. The filter may be, for example, a spectral filter to narrow the wavelength of the excitation light source. This filter could either be a colored glass filter, an interference filter (or multi-layer dielectric) or a programmable liquid crystal dielectric filter to allow tuning of the light source to different wavelengths to address different dyes.

The present apparatus may comprise an objective lens that lies between the surface of the substrate and a detector. The objective lens may be necessary in the apparatus. However, where the detector is large and can efficiently detect light emitted from any point on the array an objective lens is not required. Furthermore, an objective lens is not required where a detector very close to the array can detect a large fraction of light. The objective lens functions to focus light emitted by an irradiated target feature onto a predetermined region of a detector. Furthermore, in one embodiment the detector sees the whole surface of the array. In another embodiment there is a mapping of small regions of the sample, or slide, to different pixels of an array detector such as a CCD array. The objective lens should be highly efficient at light collection and as close to the slide as possible and, preferably, on the side of the slide that is opposite from the illumination.

The apparatus of the invention further comprise an imaging detector for detecting a response from the various features on the surface of the substrate. The response radiation may be directed to the detector by means of, for example, a dichroic beam splitter or interference filter, which passes light having a wavelength greater than a predetermined value but reflects light having a wavelength less than a predetermined value. In other words the value should be between the emission wavelength of the fluorescent dye and the excitation wavelength of the light source.

The detector may be a photodetector or light detector such as, for example, a photomultiplier tube, a photodiode, a phototransistor, a vacuum photodiode, a CCD array, a CMOS sensor, a photodiode array, an avalanche photodiode, and so forth. An array detector may be used to measure individually the signal from each light source. At least one detector element is used to measure the signal from each light source in an array. However, more than one detector may be employed to over-sample the targets permitting the discrimination against non-uniformities. One example of an array detector is a solid state semiconductor device such as charge-coupled device (CCD) array.

Instead of using an array detector to detect the light emitted, a single element optical detector may be used. To this end, either temporal multiplexing or frequency multiplexing can be done. In temporal multiplexing the light sources are activated individually and sequentially. The same detector detects light signals emitted from multiple features.

The present apparatus may be used in both confocal and non-confocal detection. The engineering decision as to whether an imaging system uses confocal or non-confocal detection depends on the dominant source of noise in the system and the tolerable levels of background light from the native fluorescence of the substrate or fluid near the surface (for wet-scanning). Confocal detection is the focussing of the beam to either a small spot or a narrow slit and the synchronous (or simultaneous) detection primarily of the region of the focal spot, usually by a single pinhole of single pixel or group of pixels. In imaging planar slides, confocal detection is useful if the background (fluorescence or phosphorescence) from the slide substrate itself is significant. Similarly, if the slide is scanned wet there is additional background from the liquid media, unbound labeled target, contaminants, or Raman. There are a number of ways to reduce these effects. In one approach the slide is scanned dry and a reflective layer is used between the substrate and the ligands binding the target on the surface. In another approach the sample can be scanned dry and a low fluorescence glass, quartz, or silica substrate is used.

As mentioned above, the approaches outlined herein can be applied to either confocal or non-confocal detection. In the case of confocal detection, a synchronous detection scheme is preferable. Independent of the type of beam scanner, the readout from the device described above could be either synchronous or non-synchronous with respect to the illumination and detection. In the non-synchronous case, the sample is illuminated over some broad region (representing many pixels), such as a linear strip and, then, the corresponding region of the detector is read out after that region is scanned. In the synchronous case, each pixel (or set of pixels) is (are) successively illuminated serially and read-out or stored serially for subsequent readout. The synchronous approach is preferred, although not necessary, for applications requiring confocal scanning in that it provides a means of spatial discrimination that makes possible confocal scanning. In other words, only detecting light from the illuminated region while minimizing the collection and detection of light originating from regions out of the focal plane or from undesired regions within the plane. The advantages of the non-synchronous approach include simplicity, low cost and ease of manufacture of the system.

For the embodiment utilizing synchronous detection, there is a mode of detection commonly used with CCD arrays called time-delayed integration (TDI). TDI is particularly useful in applications requiring rapid image acquisition under conditions of minimal lighting. In this mode, light illuminates a narrow region (or slit) of a moving target (for example a piece of paper moving on a roller) light scattered or emitted from that region of the target is collected and imaged to a narrow region of adjacent pixels of a CCD. As the target (or slide) is moved linearly the charges are synchronously shifted in the vertical registers of the CCD array from well to well. In this way charge continues to accumulate within the CCD array as the object moves across the object plane, but each point on the object maps to a moving charge packet in the array. Since there is noise associated with reading the charge from the array, but little noise associated with shifting the charge around, this is an effective way to integrate charge without adding noise.

The same approach can be used in the case of fluorescence scanning by moving the slide synchronously with the shifting of the array. In this case, a region of a surface such as a slide is illuminated, either by scanning the light across the array in a rapid sweep, while the array remains relatively stationary, or by uniformly illuminating a narrow section of the array while moving the charge across it. One of the difficulties of this approach is the high degree of uniformity required of the illumination. The illumination by a light source such as an LED, laser diode, laser, or VCEL combined with a diffractive element provides a uniform region of illumination. Furthermore, even if the illumination is not perfectly uniform, there are multiple ways for correcting for the variation. First, non-uniformities in the direction of charge motion can be averaged out by shifting the charge vertically in the CCD-array across the rectangular stationary illuminated region. Second, the residual non-uniformities along the longer axis can be measured using a uniform or homogeneous sample. The non-uniformities of the illumination can be measured, and the images can be corrected by background subtraction, followed by normalization to those images of homogeneous standards.

Another approach, which is similar to that above and does not require any mechanical degree-of-freedom, is a two-dimensional sensing device, such as a CCD-array sensor or a CMOS-array.

In one embodiment, if the sample uses a dry scanning with front-surface illumination and detection confined to a plane, then the scanner need not be confocal. It is much simpler to discriminate against unbound labeled targets in the solution, and solution Raman, or scatter from the solution, or from background fluorescence of contaminants in the solution. Similarly, if the detection is from the illumination side of the substrate, a reflective layer can be used between the probes on the surface and the substrate itself. In this case it would be unnecessary to discriminate against scatter, fluorescence or phosphorescence from within the slide substrate. There would be additional enhancements due to interferometric effects.

For enhanced operation, the plane of the surface of the array should be in the object plane of the lens. Glass microscope slides are typically warped and exhibit variations in thickness. This is especially true of cheaper substrates, such as the float glass commonly used in making disposable slides. Any variations in thickness and flatness of a system equipped with a fast lens (high NA), even a non-confocal system, will limit the effective resolution of the image and degrade the uniformity across the field of the array. In the present apparatus, autofocus can be done so that focus adjustments may be made in real time while scanning is taking place. However, with a whole array imaging system, the surface of the array lies in the focal plane and, therefore, any focussing must be done before imaging. One more passive approach is to reference the backside to a waffle-plate style vacuum chuck to make the surface of the array lay flat. This presumes that the thickness tolerances are tighter than the focal plane tolerance. This may also necessitate the use of a thinner substrate so that it can flex sufficiently easily that a partial vacuum can make it flat. Even in this case some automated focussing may be required. This could be either a single point or multi-point focus adjustment depending on the glass tolerances in thickness, wedge, and on the readers mechanical stability.

Ultimately, the tolerances for focus will depend on the speed of the lens. Decreasing the numerical aperture (and hence the speed) will increase the depth of field and focal plane tolerance. The trade-off here is that a lower numerical aperture means that less fluorescent light will be collected and longer detection time will be required. This will have at least two detrimental effects. First, the longer the scan time, the more dark current will accumulate in the sensor. Second, more photodegradation of the dye molecules themselves occurs.

Another problem related to the speed of the lens is the field distortion. High numerical aperture lenses with large fields of view tend to create significant distortion (spatial non-linearities), especially near the perimeter of the field of view. Even if the distortion does not degrade the image clarity, it will move the apparent locations of features in the image relative to their actual locations on a surface such as a slide. This effect can be corrected with feature extraction software that is commercially available.

Quantum Dot dye particles have a number of properties that make them particularly interesting for use in array detection. First, they are tunable over a wide range of wavelengths. They have a broad absorption curve, meaning that a plurality of different dye particles (at differing wavelengths) can be excited at a single wavelength, by, say, a single monochromatic light source. They are efficient emitters. The have are very photo-stable. They have fairly narrow emission bands making them amenable to being used in combination.

An additional consideration for Quantum Dot dyes is the trade-off involved in selecting the illumination areas. These dyes tend to saturate when hit with a high photon flux. They become excited into long-lived states, keeping them from being viable for many milliseconds. If they are illuminated at a lower photon flux, they will be less likely to be excited into the upper state. This means there may be an optimal illumination area for optimal detection, one that allows each quantum dot particle to be repeatedly excited in a single scan. This is a more important effect for high sensitivity to low signals where one is virtually counting individual quantum dot particles in each pixel, which can only be accomplished by efficient detection.

The apparatus of the invention may include any number of additional lens and other assemblies such as, for example, a scanning lens assembly, which functions to correct distortions due to a galvanometer scanner, a high-NA, wide FoV lens, which allows a large scan area while collecting light with high efficiency, an emission filter wheel, which functions to prevent incident light from passing to a detector, but allows tuning of the excitation an/or emission to accommodate the use of different dyes.

The excitation light from a light source impinges on the label and causes it to emit light as a signal. Only target features where a label has become bound emit light. The detected light signals are synchronized with electronic excitation for light sources and processed. By analyzing the pattern of the light signals, the identity of the targets can be determined.

A data acquisition system may be used to gather and process signals from the detector. In one embodiment data acquisition may be accomplished by means of a microprocessor device or a computer operatively connected to a detector such as a photodetector for receiving digitized or analog detector signals related to light emission level measured by the detector. The microprocessor may also be used for control of the position and movement of the diffractive element and/or any mirrors and/or the holder for the sample. The operational design of this embodiment of the apparatus is conventional and will be apparent to those skilled in the art from the operation of the apparatus as described herein.

Figure 2:
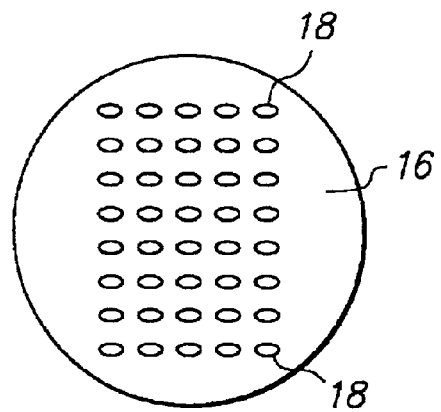
FIG. 2 is a sketch depicting a diffractive element of the apparatus of FIG. 1.
Figure 3:
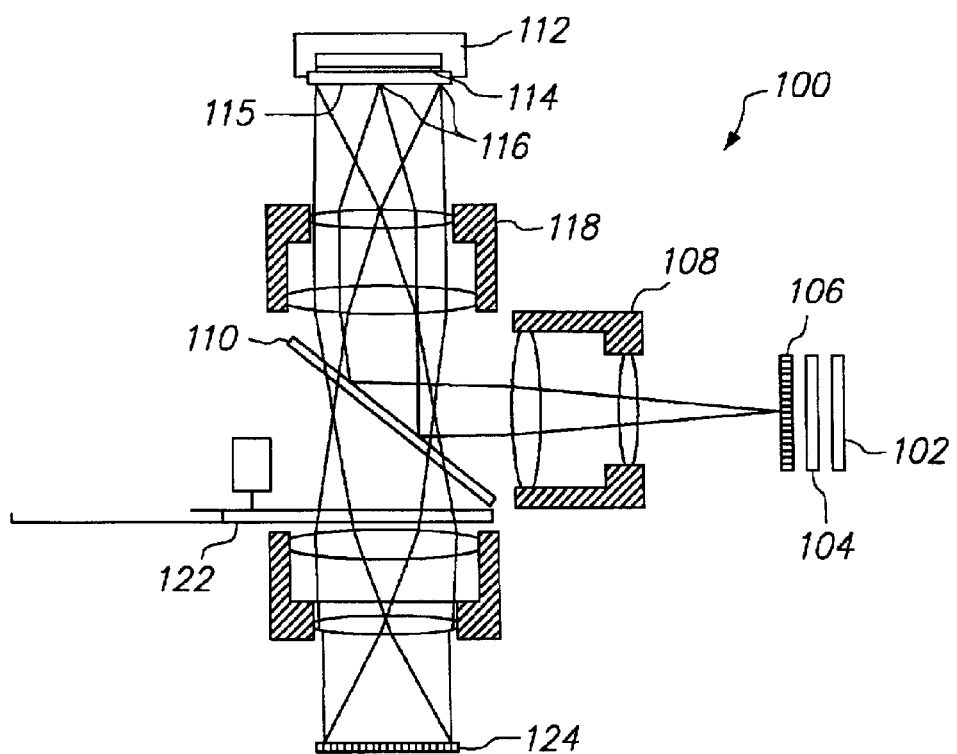
FIG. 3 is a diagrammatic sketch showing another embodiment of an apparatus in accordance with the present invention.

One embodiment of an apparatus in accordance with the present invention is shown in FIG. 1 by way of illustration and not limitation. Apparatus 10 comprises light source 12 and beam expander 14, which is disposed adjacent to light source 12 and between light source 12 and diffractive element 16. In the embodiment of FIG. 1 diffractive element 16 is a disk having a plurality of openings (see FIG. 2). Apparatus 10 further comprises holder 20, which holds substrate slide 22, which comprises a number of features 24 on surface 23 of slide 22. Objective lens 26 lies between substrate slide 22 and detector 28 and includes emission filter 27, which blocks excitation light scattered by the substrate. Emission filter 27 may be an interference filter (multi-layer dielectric). For a high numerical aperture system with near 1:1 optics, the filter is usually positioned between two symmetrically placed identical (or nearly so) high-NA lenses. Alternatively, the filter may be positioned between the lens and the array detector if the distance is longer than the distance from the lens to the substrate. Emission filter 27 may be an emission filter wheel such as depicted in FIG. 3. Diffractive element 16 is driven by motor 30. The operation of apparatus 10 is controlled by a microprocessor device (not shown), which also comprises a data acquisition system.

Apparatus 10 may be used to image a plurality of features 24 on slide 22. Light from light source 12 is directed through beam expander 14 through one or more openings 18 in diffractive element 16. Depending on the position of diffractive element 16, the light is directed to illuminate features 24 on slide 22. In particular, any label present at a feature site 24 is activated and emits a light signal that is directed to objective lens 26, which focuses the emitted light to a predetermined position 32 on detector 28. Motor 30 drives diffractive element 16 so that light from light source 12 is directed to one or more different features 24. The process is repeated until all of the features 24 on slide 22 have been illuminated.

As indicated above, the apparatus of the invention may be used for scanning a plurality of sample features on the surface of a substrate such as, for example, an array, e.g., planar microarray, of sample regions, to detect and optionally, to quantitate, detectable reporter groups localized in one or more of the sample regions. As one example, the substrate microarray may be a high density, two-dimensional array of oligonucleotides of different sequences that are suitable for use in sequencing by hybridization or detection of mutational forms of an analyte nucleic acid. A solution of fluorescent-labeled nucleic acid analyte is placed on the microarray under selected stringency conditions, leading to hybridization of the analyte with complementary-sequence oligonucleotides in the array, and fluorescent labeling in the array regions where such binding occurs. The substrate is then washed to remove unbound and non-specifically bound analyte.

As another example, a microarray may be prepared to include a high-density array of polypeptides of different sequences, which collectively make up a combinatorial peptide library. To this array is added a fluorescent-labeled receptor or anti-ligand analyte, which may bind with high affinity to one or more of the library members. After exposing the array to the labeled target, the surface is washed to remove unbound and weakly bound target, leaving fluorescent labeling at high-affinity regions of the microarray only. Other types of one- or two-dimensional microarrays, such as small molecule library arrays, arrays of single clonal cells, and the like are also suitable.

In one embodiment of a substrate array of sample target features, the features are exposed to probes that are labeled with a fluorescent group. After fluorescent labeling, the substrate is placed on a holder such as, e.g., a microscope stage, for scanning and fluorescence-position mapping using an apparatus in accordance with the present invention. In the configuration shown in FIG. 1 substrate slide 22 is a transparent glass slide having a microarray formed on its surface 23, consisting of a two-dimensional array of features 24. Each feature 24 shown is a member of a linear array. The beam diagrams in FIG. 1 show illumination beam may be focused by opening 18 in diffractive element 16 to achieve high resolution, meaning that the illumination spot at the plane of the microarray is substantially smaller than the dimensions of an array region. High beam resolution can be achieved in the present invention with relatively inexpensive parts.

Arrays suitable for binding to targets may be prepared in a number of different ways. As an illustration, biopolymer arrays, such as arrays comprising polynucleotides, polypeptides, polysaccharides and the like and mixtures thereof, can be made by in-situ synthesis of a biopolymer on a substrate or by deposition of a previously made biopolymer onto the substrate to form features of an array. For example, in-situ synthesis methods include those for making peptide arrays as described in U.S. Pat. No. 5,449,754 and for making polynucleotides as described in PCT publication WO 98/41531. On an array, different locations can be made to have different biopolymers. For example, the method described by Khrapko, et al., *DNA Sequence* (1991) 1:375–388 can be used to make DNA arrays by spotting DNA onto the surface of a substrate with a micro pipette. Also, a vacuum manifold can be used to transfer aqueous DNA samples from a plurality of wells to a substrate surface. In yet another method, a pin or capillary can be used to dip into a fluid sample of a biopolymer and then touch the substrate surface. By using a number of pins or capillaries, a plurality of samples can be spotted onto the substrate surface. In another method of making biopolymeric arrays, biopolymeric agents are "grown" on the surface of a substrate in discreet regions. See, for example, U.S. Pat. No. 5,143,854 and Fodor et al., *Science* (1991) 251:767–773. In yet another method of producing nucleic acid arrays, inkjets can be used to deposit nucleic acids on the substrate surface (see, for example, U.S. Pat. No. 5,658,802. U.S. Pat. No. 5,338,688 describes the use of a bubble-jet for similar applications. Other than using synthesized probe or binder molecules that are bound to an array substrate, naturally occurring molecules, fragments thereof, or complements of the molecules or fragments thereof may be used. This is particularly useful if a large number of target chemicals, or fragments the chemical structures of which are not known precisely, are to be used as probes. Automated devices for depositing nucleic acids on a substrate surface, e.g. for producing nucleic acid arrays, as well as for depositing various chemicals in an array are known in the art.

Another embodiment of an apparatus in accordance with the present invention is depicted in FIG. 3. Apparatus 100 comprises light source 102, excitation filter 104 and diffractive element 106. An optional scanning lens 108 is located between diffractive element 106 and dichroic mirror 110. Apparatus 100 further comprises holder 112, which holds substrate slide 114, which comprises a number of features 116 on surface 115 of slide 114. Apparatus optionally comprises high-NA, wide FoV lens 118 between mirror 110 and substrate 114. Also optionally included is emission filter wheel 122 for preventing incident light. Apparatus 100 further comprises array detector 124. Diffractive element 106 is driven by a motor (not shown). The operation of apparatus 100 is controlled by a microprocessor device (not shown), which also comprises a data acquisition system.

All publications and patent applications cited in this specification are herein incorporated by reference as if each individual publication or patent application were specifically and individually indicated to be incorporated by reference.

Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims. Furthermore, the foregoing description, for purposes of explanation, used specific nomenclature to provide a thorough understanding of the invention. However, it will be apparent to one skilled in the art that the specific details are not required in order to practice the invention. Thus, the foregoing descriptions of specific embodiments of the present invention are presented for purposes of illustration and description; they are not intended to be exhaustive or to limit the invention to the precise forms disclosed. Many modifications and variations are possible in view of the above teachings. The embodiments were chosen and described in order to explain the principles of the invention and its practical applications and to thereby enable others skilled in the art to utilize the invention.

What is claimed is:

1. An imaging apparatus comprising:
   (a) a holder for a surface,
   (b) a light source adapted to illuminate said surface,
   (c) a diffractive element between said holder and said light source, said diffractive element comprising an array of diffraction gratings wherein said diffractive element is arranged to sequentially illuminate different sets of features on said surface having a sample deposited thereon until substantially all of the features on said surface are illuminated and
   (d) an imaging detector adapted to receive light from said surface.

2. An apparatus according to claim 1 wherein said light source is a laser, a focused lamp or an LED.

3. An apparatus according to claim 1 wherein said diffractive element is a spinning disk, a rotating drum or a rectilinear array.

4. An apparatus according to claim 1 wherein said diffractive element is synchronized to a said detector.

5. An apparatus according to claim 1 wherein said diffractive element is non-synchronized to said detector.

6. An apparatus according to claim 1 wherein said imaging detector is a solid state detector.

7. An apparatus according to claim 6 wherein said solid state detector is a CCD array, a CMOS array, a diode array or a PIN-diode array.

8. An apparatus according to claim 1 further comprising a focusing element.

9. An apparatus according to claim 1 further comprising an objective lens.

10. An apparatus according to claim 1 wherein said diffractive element is movable.

11. An apparatus according to claim 10 wherein said diffractive element is driven by a motor.

12. A method for imaging a surface comprising a plurality of discrete features, said method comprising:
    (a) selectively diffracting light on to a set of one or more predetermined features of said surface at a predetermined point in time and detecting light from said surface,
    (b) repeating step (a) for different sets of one or more predetermined features until substantially all of the features on said surface are illuminated to thereby image said surface.

13. A method according to claim 12 wherein said light detected is fluorescence.

14. A method according to claim 12 wherein said discrete features are polynucleotides.

15. A method according to claim 12, which comprises selectively directing light from a light source on to regions of a diffractive element disposed with respect to said surface such that one or more predetermined features of said surface are illuminated at a predetermined point in time wherein said diffractive element comprises an array of diffraction gratings and wherein said diffractive element is arranged to illuminate a set of separate pixel regions of a sample on the surface at one predetermined point in time and to illuminate another set of different pixel regions of said sample at another predetermined point in time.

16. A method according to claim 15 wherein said diffractive element is a disk, drum or rectilinear array.

17. A method according to claim 15 wherein said diffractive element is driven by a motor.

18. A method according to claim 15 wherein said selectively directing light comprises moving said diffractive element with respect to a stationary light source.

19. A method according to claim 15 wherein said selectively directing light comprises moving said light source with respect to a stationary diffractive element.

20. A method according to claim 12 wherein said detecting is carried out using a solid state detector.

21. An imaging apparatus comprising:
    (a) a holder for a surface,
    (b) an array of light sources adapted to illuminate said surface,
    (c) a diffractive element between said holder and said light sources, said diffractive element comprising an array of openings and
    (d) an imaging detector adapted to receive light from said surface.

* * * * *